United States Patent [19]

Higashio et al.

[11] Patent Number: 5,658,742

[45] Date of Patent: Aug. 19, 1997

[54] MONOCLONAL ANTIBODY

[75] Inventors: Kanji Higashio, Kawagoe; Nobuyuki Shima, Oyama; Fumiko Oogaki, Utsunomiya, all of Japan

[73] Assignee: Snow Brand Milk Products Co., Ltd., Japan

[21] Appl. No.: 404,643

[22] Filed: Mar. 15, 1995

[30] Foreign Application Priority Data

Mar. 18, 1994 [JP] Japan ................................. 6-074263

[51] Int. Cl.$^6$ .................... G01N 33/53; G01N 33/542; G01N 33/567; C07K 16/00
[52] U.S. Cl. .................. 435/7.9; 435/7.21; 435/7.23; 435/330; 435/331; 436/63; 436/64; 530/388.2; 530/388.8; 530/387.7; 530/387.9
[58] Field of Search ................ 435/7.23; 436/501, 436/64; 530/387.1, 387.7, 388.1, 388.24

[56] References Cited

FOREIGN PATENT DOCUMENTS

| 0519728 A2 | 12/1992 | European Pat. Off. ........ C12P 21/08 |
| 0519728A2 | 12/1992 | European Pat. Off. ........ C12P 21/08 |

OTHER PUBLICATIONS

E. Gohda et al., "Purification and Partial Characterization of Hepatocyte Growth Factor from Plasma of a Patient with Fulminant Hepatic Failure" *J. Clin. Invest.* 81:414–419 (1988).

K. Matsumoto et al., "Roles of HGF as a Pleiotropic Factor in Organ Regeneration", Hepatocyte Growth Factor–Scatter Factor (HGF–SF) and the *C–Met* Receptor, ed. I.D. Goldberg and E.M. Rosen, Birkhauser Verlag, Basel, Switzerland (1993).

K. Miyazawa et al., "Molecular Cloning and Sequence Analysis of cDNA for Human Hepatocyte Growth Factor" *Biochem. and Biophys. Res. Comm.* 163(2):967–973 (1989).

T. Seki et al., "Isolation and Expression of cDNA for Different Forms of Hepatocyte Growth Factor from Human Leukocyte" *Biochem. and Biophys. Res. Comm.* 172(1):321–327 (1990).

N. Shima et al., "Hepatocyte Growth Factor and Its Variant with a Deletion of Five Amino Acids Are Distinguishable in Their Biological Activity and Tertiary Structure" *Biochem. and Biophys. Res. Comm.* 200(2):808–815 (1994).

G. Shiota et al., "Hepatocyte Growth Factor Inhibits Growth of Hepatocellular Carcinoma Cells" *Proc. Natl. Acad. Sci. USA* 89:373–377 (1992).

H. Tajima et al., "Hepatocyte Growth Factor Has Potent Anti–Proliferative Activity in Various Tumor Cell Lines" *FEBS* 291(2):229–232 (1991).

K.M. Weidner et al., "Evidence for the Identity of Human Scatter Factor and Human Hepatocyte Growth Factor" *Proc. Natl. Acad. Sci. USA* 88:7001–7005 (1991).

N. Shima et al., "ELISA for F–TCF (human hepatocyte growth factor/hHGF)/fibroblast–derived tumor cytotoxic factor antigen employing monoclonal antibodies and its application to patients with liver diseases" *Gastroenterologia Japonica* 26(4):477–482 (1991).

Rubin et al, "A broad–spectrum human lung fibroblast––derived mitogen is a variant of hepatocyte growth factor" *PNAS*, vol. 88, pp. 415–419. Jan. 1991.

Smith et al, "Pitfalls in the use of ELISA to screen for monoclonal antibodies raised against small peptides" *J. of Immunol. Methods*, vol. 158, pp. 151–160 1993.

Shima et al., "Cytotoxic Factor/Hepatocyte Growth Factor from Human Fibroblasts: Cloning of Its cDNA, Purification and Characterization of Recombinant Protein" *Biochem. and Biophys. Res. Comm.* 180 No. 2:1151–1158 (1991).

K. Matsumoto et al., "Deletion of Kringle Domains or the N–Terminal Hairpin Structure in Hepatocyte Growth Factor Results in Marked Decreases in Related Biological Activities" *Biochem. and Biophys. Res. Comm.* 181 No. 2:691–699 (1991).

*Primary Examiner*—Lila Reisee
*Assistant Examiner*—Yvonne Eyler
*Attorney, Agent, or Firm*—Testa, Hurwitz & Thibeault, LLP

[57] ABSTRACT

This invention relates to a monoclonal antibody having affinity to human TCF-II without any affinity to HGF and determination or purification methods of TCF-II using the antibody. The monoclonal antibody can be obtained by adding a blocking solution containing a surface active agent to the culture medium containing monoclonal antibody to block antibodies other than said monoclonal antibody, followed by reaction with a solid phase antigen, TCF-II. Human TCF-II can be selectively and effectively purified or determined without any influence of the presence of HGF by using the antibody.

7 Claims, 2 Drawing Sheets

1

MONOCLONAL ANTIBODY

FIELD OF THE INVENTION

This invention relates to a novel monoclonal antibody having affinity with human TCF-II without any affinity with human hepatocyte growth factor (HGF) and preparation thereof. Furthermore, the present invention relates to specific determination and purification of TCF-II using the antibody without any disturbance of the co-existing HGF.

BACKGROUND OF THE INVENTION

β-Interferon has been well known as a tumor cytotoxic factor which is produced by human derived fibroblasts. Physiologically active factors produced by fibroblast cells have been disclosed in Japanese Laid-open Patent Application Nos. 146,293 (1983), 1,872 and 33,120 (1986), 103021 (1987) and 10998 (1989). On the process of investigation of antitumor protein derived from fibroblasts, the inventors of the present invention have found antitumor protein, being quite different from proteins previously reported and succeeded in cloning the cDNA coded for the novel protein. The inventors identified total amino acid sequence and confirmed the usefulness thereof. The novel antitumor protein and gene thereof were disclosed in WO 90/10651 and named TCF-II. Total amino acid sequence of the protein deduced from the cDNA sequence is shown in Sequence Table No. 1.

TCF-II has both potent antitumor activity and growth stimulation activity for normal cells, and was confirmed as a member of the family of hepatocyte growth factor (HGF). TCF-II shows molecular weight of 78,000±2,000 or 74,000±2,000 in SDS-polyacrylamide gel electrophoresis (SDS-PAGE). Under reducing conditions, TCF-II shows a common A band with molecular weight of 52,000±2,000 and a band B with molecular weight of 30,000±2,000 or a band C with molecular weight of 26,000±2,000. The monoclonal antibodies against TCF-II had been disclosed in Japanese Laid-open Patent Application No. 97 (1993) and the inventors of the present invention found that the antibodies equally recognize both TCF-II and HGF during the investigation of the present invention.

TCF-II and HGF have different biological activities and their differentiation is necessary. However, TCF-II and HGF have very similar amino acid sequences and their respective antibodies exhibit cross reactivity each other. No specific epitope of TCF-II has been obtained, therefore, no monoclonal antibody which exhibits affinity solely with TCF-II without any affinity with HGF has been obtained.

The present inventors noticed the usefulness of TCF-II and have been investigated the application to an antitumor agent and a wound healing agent, and the use as a marker for the diagnosis of diseases.

There is a marked difference in biological activities between TCF-II and HGF. HGF is respectively about 28-, 10- and 2-fold more potent than TCF-II in specific activity for stimulating growth of human umbilical vein endothelial cells (HUVEC), human aorta smooth muscle cells (AOSMC), and murine myeloblastic cell line (NFS-60) (Goto et al.: SEIKAGAKU published by the Japanese Biochemical Society, 65(8) 835, 1993). While, TCF-II is respectively about 1.4- to 1.9-fold more potent than HGF in specific activity for stimulating growth of rat hepatocytes (Shima et al.: Biochem. Biophys. Res. Commun., 180, 1,151–1,158, 1991; Matsumoto et al.: ibid., 181, 691–699, 1991) and about 3- fold more potent than HGF in specific activity for stimulating growth of pig kidney epithelial cells (LLCPK-1) (Goto et al.: SEIKAGAKU, 65(8) 835, 1993, published by the Japanese Biochemical Society). Therefore, selective and quantitative determination of TCF-II and HGF is very useful to investigate their excretion ratio in human cell culture, and differences in their secretion sites and physiological roles in body, and the relationship between the blood concentrations of TCF-II or HGF, and disease conditions.

However, TCF-II and HGF have high homology each other, and selective and quantitative determination of TCF-II in samples containing both TCF-II and HGF such as human cell culture, serum or plasma can be carried out only by a bioassay using difference of biological activity in target cells between TCF-II and HGF as described above. Furthermore, the accurate and precise quantitative determination was difficult by the bioassay. At present, immunoassay is a main method for the determination of very small amount of substances and an antibody suitable for the selective determination of TCF-II, that is, a monoclonal antibody which reacts only with TCF-II, but not with HGF, has been desired. The detection of secretion sites of TCF-II in human tissue can be effectively performed by application of such an antibody, and affinity chromatography using such antibody makes it possible to specifically purify and effectively recover TCF-II from human cell culture containing both TCF-II and HGF.

However, TCF-N and HGF have similar amino acid sequences. Heretofore, conventional immunization of an animal to provide antibody producing cells, followed by cell fusion to prepare hybridoma could not screen a cell line for the production of an antibody which selectively recognize TCF-II. Thus, no antibody which recognize only TCF-II has been obtained.

SUMMARY OF THE INVENTION

The object of the invention is to provide a novel monoclonal antibody having selective affinity only to TCF-II without affinity at all to HGF.

The other object of the present invention is to provide selective determination and purification methods of TCF-II without any disturbance of HGF under the concurrent presence of human HGF.

The novel monoclonal antibody of the present invention can be selected by diluting the culture broth of a hybridoma, which produce the anti-TCF-II antibody that reacts only with TCF-II without any reactivity with HGF, to 2- to 4-fold with a blocking solution. The culture broth diluted with block solution was added to well with each solid phase antigen (immobilized TCF-II or HGF), followed by screening of antibody producing hybridoma which exhibits affinity only to TCF-II without any affinity to HGF. The screened clone is cultured to give the novel monoclonal antibody of the present invention.

DETAILED DESCRIPTION OF THE INVENTION AND PREFERRED EMBODIMENT

Figure 1:
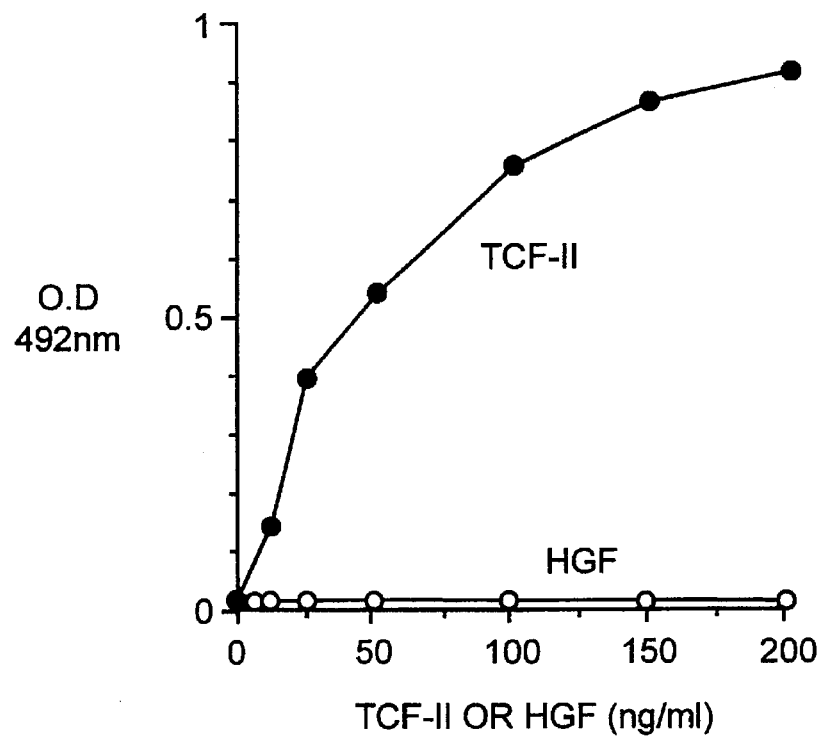
FIG. 1 shows the determination curves of TCF-II and HGF with the combination of antibody A2G5 of Example 6 and POD-labeled 3P2D6.
Figure 2:
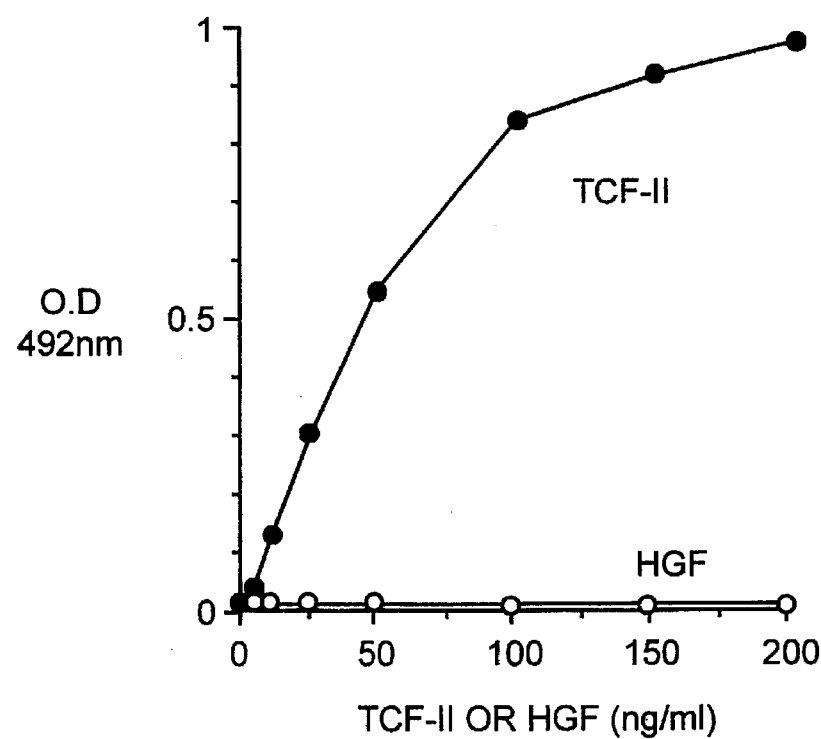
FIG. 2 shows the determination curves of TCF-II and HGF with the combination of antibody H9E3 of Example 6 and POD-labeled 3P2D6.
Figure 3:
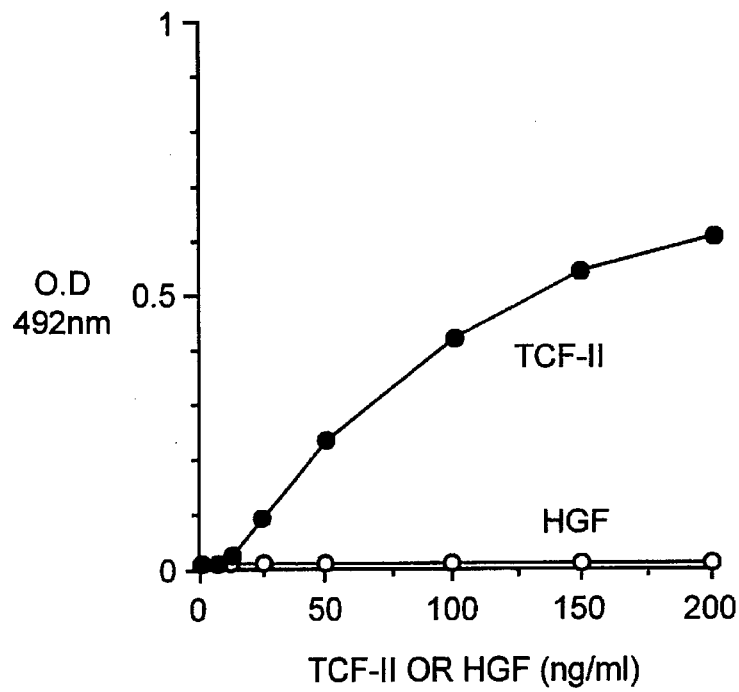
FIG. 3 shows the determination curves of TCF-II and HGF with the combination of antibody C10D1 of Example 6 and POD-labeled 3P2D6.

The antibody of the present invention and a process for the preparation thereof are shown below.

The monoclonal antibody of the present invention can be prepared according to a conventional method for the preparation of monoclonal antibody using TCF-II as an antigen.

TCF-n as an antigen can be obtained by the method disclosed in aforementioned WO 90/10651. Particularly, TCF-II may be prepared by culturing microorganisms or the other animal cells constructed by a gene engineering based on the oligonucleotide sequence of TCF-II gene disclosed in the aforementioned WO 90/10651. Even TCF-II, which is not highly purified, can be used as an antigen.

Immunized lymphocytes obtained by immunization of mammals with the antigen or by an in vitro immunization method are fused with myeloma of mammals to give hybridoma. The obtained hybridoma is cultured and the resultant cultured medium was screened using highly purified TCF-II or HGF as an antigen to select hybridoma producing or secreting monoclonal antibody which reacts only with TCF-II without any reactivity with HGF. The screened clones were cultured to give the aimed antibody.

Any mammals can be used for the preparation of the hybridoma, but small animals such as mice and rats are generally used. TCF-II is suitably diluted with a saline solution or the like and intravenously or intraperitoneally administered to the animals with an adjuvant, if necessary, for 2–5 times every 2–20 days. The immunized animal was killed and laparotomized three days after final immunization, the spleen was taken out and the spleen cells were used as immunized B lymphocytes.

Myeloma cells derived from mouse for cell fusion with the immunized B lymphocytes include, for example, p3/× 63-Ag8, p3-U1, NS-1, MPC-11, SP-2/0, F0, P3×63 Ag 8. 653 and S194. Rat derived R-210 cells may also be used. Human B lymphocytes were immunized by an in vitro immunization method and were fused with human myeloma cells or transformed human B lymphocytes with EB virus, which were used as a parent cell line, to produce human type antibody.

Fusion of the immunized B lymphocytes and the transformed B cell line is carried out principally by known methods. For example, the method of Koehler, G. et al, (Nature, 256, 495–497 (1975)) is generally used, but an electric pulse method can also be applied. The immunized B lymphocytes and transformed B cells are mixed at conventional ratios and a FCS-free cell culture medium containing polyethylene glycol is generally used for cell fusion. The fused cells are cultured in HAT selection medium containing FCS to screen hybridoma.

For screening of hybridoma producing antibody which is solely reactive with TCF-II without any reactivity with HGF, ELISA, plaque assay, Ouchterlony or agglutination assay can be principally adopted. Among them, ELISA is simple and easy to operate with sufficient accuracy and generally used. However, mere application of conventional antibody detection methods could not lead to success in screening of the antibody producing hybridoma of the present invention due to the non-specific background in the screening of these cells. HGF and TCF-II have similar structures and the presence various mouse IgGs in the culture medium causes to bind non-specifically to TCF- II or HGF antigen, and disturbed the identification of specific binding of antigen and antibody. Mouse IgG which is reactive with HGF antigen binds non-specifically to TCF-II. Furthermore, some hybridomas produce mouse IgGs against many other antigens in addition to mouse IgG against TCF-II or HGF. Those mouse IgGs bind non-specifically to immobilized HGF or TCF-II. These non-specific bindings make it difficult to screen hybridoma producing antibody which has affinity solely to TCF-II without any affinity to HGF. In the present invention, ELISA was improved to strictly screen hybridoma producing monoclonal antibody which shows affinity to TCF-II and without any affinity to HGF and the improved ELISA made it possible to obtain monoclonal antibody producing hybridoma of the present invention. The improvement of ELISA has following characteristic features.

Screening of hybridoma producing monoclonal antibody, which reacts only with TCF-II without any reactivity with HGF, using conventional ELISA or the other methods, is difficult. Therefore, no successful screening method has been found because of the non-specific adsorption of various mouse IgGs in culture medium of the hybridoma as shown above.

The inventors found a method that various IgGs in the culture medium produced by hybridomas do not influence the screening of TCF specific antibody. In the present invention, a solid phase ELISA was improved to strictly screen antibody which exhibits affinity only to TCF-II without any affinity to HGF, and led to success in obtaining the antibody of the present invention. That is, in the conventional solid phase ELISA in which the culture medium of hybridoma is directly added to well coated with an antigen (TCF-II ) and is directly caused to react with the antigen. TCF-II reactive antibody producing hybridoma is easily selected by screening hybridoma having intensive coloration (optical density) after POD enzymatic reaction. However, various mouse IgGs against TCF-II, HGF and the other antigens also non-specifically binds to the immobilized TCF-II or HGF and this non-specific binding affect the subsequent reaction detecting mouse IgG which exhibits solely affinity to TCF-II without any affinity to HGF or other antigens. Thus, the selection by the coloration after POD enzymatic reaction becomes difficult to identify whether the coloration was caused by TCF-II specific antibody or not. In the present invention, therefore, hybridoma culture medium is diluted 2- to 4-fold with a blocking solution containing 0.1% Tween$^{RTM}$ 20, for example, 2% bovine serum albumin (BSA) or 25–50% Blockace$^{RTM}$ (Snow Brand Milk Products Co. Ltd.), and added to the solid phase antigen to prevent non-specific binding of co-existing mouse IgGs to the antigen and to make screening of antibody producing hybridoma, which exhibits affinity only to TCF-II without any affinity to HGF, possible.

Stable antibody producing cell line is established by screening of hybridoma obtained by the improved ELISA of the present invention followed by cloning 3–5 times with limiting dilution using the ELISA of the present invention. The established hybridoma can be subcultured by conventional methods and kept under freezing, if required. The hybridoma is cultured by known methods or the hybridoma is transplanted in abdominal cavity of mammals and culture broth is recovered as ascite. Monoclonal antibody in the recovered cultured broth can be purified by conventional methods such as salting out, gel filtration, protein A or G affinity chromatography.

The resultant antibody reacts only with TCF-H without any reactivity with HGF and can be used for the selective determination and purification of TCF-II. In selective determination of TCF-II, radioactive isotope-labeled or enzyme-labeled anti-TCF-II specific antibody can be used for the assay system known as radioimmunoassay (RIA) or enzyme immunoassay (EIA). Particularly, the antibody obtained by the present invention exhibits quite the same affinity to TCF-II and a TCF-II mutant which is prepared by protein engineering and has a deletion of all four N-linked oligosaccharide chains of TCF-II. However, the antibody obtained by the present invention shows no reactivity with structurally broken TCF-II in molecule in which the S—S bond is cleaved by the treatment with a reducing agent such as 2-mercaptoethanol or dithiothreitol as well as the case of HGF. This indicates that the antibody obtained by the present invention is not an antibody which recognizes the peptide sequence and sugar chain in the TCF-II protein molecule. These facts also indicate that the antibody obtained by the present invention recognizes epitope(s) which is three dimensionally formed in TCF-II molecule only. While, HGF has no such three dimensionally formed epitope.

That is, the antibody of the present invention recognizes the difference in tertiary structure between TCF-II and HGF. Therefore, it is impossible to obtain such antibody which recognizes an epitope, being formed three dimensionally in TCF-II molecule only, by immunization of mammals with HGF purified from plasma of patients with fulminant hepatic failure (Gohda et al.: Exp. Cell Res., 166, 139–159, 1986) or recombinant HGFs obtained by expression of HGF cDNAs (Nakamura et al.: Nature, 342, 440–443, 1989; Miyazawa et al.: Biochem. Biophys. Res. Commun., 163, 967–973, 1989) followed by repeating preparation and selection of hybridoma as same as the present invention. That is, although a monoclonal antibody of HGF was disclosed in Japanese Examined Patent Application No. 60359 (1993), all monoclonal antibodies against HGF can not recognize epitope(s) which is three dimensionally formed in TCF-II molecule only and is recognized by the antibody of the present invention.

The antibody of the present invention was confirmed to recognize the epitope which exists only in TCF-II. Thus, the antibody of the present invention can be used as a solid phase antibody, and an antibody which recognizes the other epitope of TCF-II as an enzyme-labeled antibody for sandwich immunoassay to specifically determine the amount of TCF-II. For example, monoclonal antibody disclosed in Japanese Laid-open Patent Application No. 97 (1993) or an antibody which recognizes common epitopes of TCF-II and HGF can be used as an enzyme labeled antibody for sandwich immunoassay. The determination system can easily and sensitively determine only TCF-II in samples such as blood or urine, and cell culture medium.

Purification of TCF-II using the antibody of the present invention can be easily carried out by affinity chromatography prepared by immobilizing an antibody with slightly higher dissociation constant ($10^{-6}$–$10^{-7}\mu$) to Affigel$^{RTM}$ 10 (BioRad Co., Ltd.).

The present invention provides a novel monoclonal antibody which exhibits affinity solely to TCF-II without any affinity to HGF. The present invention also provides a selective purification and determination methods of TCF-II under the presence of HGF by using the novel antibody.

The present invention will be explained by the following Examples, however, the scope of the invention is not restricted by these Examples.

EXAMPLE 1

Preparation of TCF-II Antigen for for Immunization and ELISA, and HGF Antigen for ELISA Expression vectors of TCF-II and HGF cDNA were constructed by inserting a 2.4 kb fragment of mouse dehydrofolate reductase (DHFR) transcription unit into plasmid pcDNA1 at Nhe I site and inserting TCF-II cDNA disclosed in WO 90/10651 or 2.3 kb of HGF cDNA (BBRC, 163, 967–973, 1989) cloned by Miyazawa et al. into the down stream of cytomegalovirus (CMV) promoter of plasmid pcDNA1. The constructed TCF-II cDNA or HGF cDNA expression vector (10 µg) and pSV2neo (1 µg) were co-transfected to Namalwa cells by the liposome mediated transfection method using lipofetin. The transformed cells were selected by G418 resistance and subsequently gene-amplified with methotrexate (MTX). TCF-II or HGF highly productive cell line was cultured in a roller bottle (two-liter volume) containing 1 L of DMEM medium supplemented with 5% calf serum (CS) at 37° C. for seven days at a rate of two rpm. Altogether 20 roller bottles for each cell line were prepared and incubated in the same way, and about 21 L of cultured medium of each cell line was obtained.

Each cultured medium contained five mg/L of TCF-II and four mg/L of HGF. TCF-II or HGF in the culture medium (20 L) was purified by column chromatographies composed of three steps such as CM Sephadex$^{RTM}$ C-50 (Pharmacia), Mono S column-FPLC (Pharmacia) and heparin 5-PW (TOSOH Co., Ltd.)- FPLC, modified slightly the method of Higashio et al. (Higashio et al.: BBRC, 170, 397–404, 1990) and pure TCF-II and HGF, which were electrophoretically homogenous, were obtained with about 60% yield, respectively.

EXAMPLE 2

Preparation of Hybridoma and Screening of Hybridoma Producing Antibody which React Solely with TCF-II Without any Reactivity with HGF Purified TCF-II obtained by Example 1 was dissolved in PBS at a concentration of 100 µg/100 µl. Balb/c mice were immunized by administrating this solution intraperitoneally three times every two weeks. In the first and second immunization, the emulsion composed of an equal volume of TCF-II and Freund's complete adjuvant was administered. Three days after the final administration, the spleen was taken out, B lymphocytes were isolated and fused with mouse myeloma P3×63-AG8.653 cells according to the method of Koehler et al. (Koehler, G., et al.: Nature, 256, 495–497, 1975). Then the fused cells were cultured in HAT medium and selected.

Conventional solid ELISA does not lead to success in selection of hybridoma producing anti-TCF-II antibody which exhibits affinity solely to TCF-II without any affinity to HGF. Then, the solid phase ELISA was modified to strictly select a hybridoma producing antibody which exhibits affinity solely to TCF-II without any affinity to HGF in the present invention and the modification led to success in obtaining the antibody of the present invention. That is, conventional solid phase ELISA composed of direct reaction of cultured medium of hybridoma to a solid phase TCF-II antigen can easily screen a TCF-II reactive antibody producing hybridoma. However, mouse IgG in hybridoma cell culture medium which specifically recognizes TCF-II specifically tends to non-specifically bind to a solid phase HGF antigen or mouse IgGs which recognize antigens other than TCF-II also non-specifically bind to a solid phase TCF-II or HGF antigen. Therefore, screening of antibody producing hybridoma with POD-labeled anti-mouse IgG antibody resulted in positive reactions in culture media of many hybridomas, although there is some differences in binding potentials. Therefore, selection of TCF-II specific antibody producing hybridoma was difficult. In the present invention, to control non-specific binding, hybridoma culture medium was diluted 2- to 4-fold with a blocking solution containing 0.1% Tween$^{RTM}$ 20 (for example, 2% BSA or 25–50% Blockace$^{RTM}$) and caused to react with the solid phase antigen. Thus, screening of hybridoma producing antibody which has affinity only to TCF-II without any affinity to HGF became possible. That is, 100 µl of purified TCF-II (10 µg/ml in 0.1M NaHCO$_3$) obtained by Example 1 was added to each well in the half (Nos. 1–6×columns A–H) of 96-well immunoplates (Nunc Co., Ltd.), then 100 µl of purified HGF (10 µg/ml in 0.1M NaHCO$_3$) obtained by Example 1 was added to each well in the remained half (Nos. 7–12×columns A–H) of the plates, and the each antigen was immobilized by incubating the plates overnight at room temperature. The wells coated with each antigen were blocked with 200 µl of 50% Blockace$^{RTM}$ (Snow Brand Milk Products Co., Ltd.) for one hour. After each well was washed three times with a washing buffer, PBS containing 0.1% Tween$^{RTM}$ 20, 100 µl each of the hybridoma culture medium diluted 2- to 4-fold with a blocking solution containing 0.1% Tween$^{RTM}$ 20 (for example, 40% Blockace$^{RTM}$) was added to each well coated with TCF-II or HGF in conventional ELISA, and incubated at 37° C. for three hours., though conventional 100 µl of each hybridoma culture medium was directly added to each well coated with TCF-II or HGF. After three hours incubation, each well was washed four times with the washing buffer. For detection of the antibody (mouse IgG) bound to TCF-II or HGF, 100 µl of peroxidase (POD)-labeled goat antimouse IgG(γ) monoclonal antibody (Cappel Co., Ltd.) diluted 1,000-fold with PBS containing 10% Blockace$^{RTM}$ and 0.1% Tween$^{RTM}$ 20 was added to each well in 96-well immunoplates, and the immunoplates were incubated at 37° C. for 2 hrs. After each well was washed three times with the washing buffer, 100 µl of an enzyme substrate solution (0.1M citrate-phosphate buffer containing 0.4 mg/ml of o-phenylenediamine.HCl and 0.006% of H$_2$O$_2$, pH 4.5) was added to each well and incubated at 37° C. for 15–30 min. The enzymatic reaction was terminated by the addition of 50 µl of 6N H$_2$SO$_4$ to each well. The optical density of each well was determined at 492 nm with an immunoreader (Corona Co. Ltd.). The effects of the modified solid phase ELISA of the present invention and a conventional solid phase ELISA on the discrimination of anti-TCF-II specific antibody were compared using culture medium of hybridoma H9E3 producing the antibody in the present invention, which was established by screening and by cloning four times using the modified ELISA of the present invention. The results are shown in Table 1.

TABLE 1

Selective effects of the improved ELISA of the present invention and conventionally used solid ELISA on screening of anti-TCF- II specific antibody using culture media of various clones obtained at 4th cloning of hybridoma, H9E3 producing the antibody of the present invention.

| Clone of H9E3 | ELISA-1 | | ELISA-2 | |
|---|---|---|---|---|
| cell line | TCF- II | HGF | TCF- II | HGF |
| No. 1 | 0.924 | 0.020 | 1.083 | 0.456 |
| No. 2 | 0.918 | 0.020 | 1.077 | 0.658 |
| No. 3 | 1.106 | 0.035 | 1.100 | 0.450 |
| No. 4 | 0.732 | 0.013 | 1.061 | 0.512 |
| No. 5 | 0.730 | 0.015 | 1.060 | 0.224 |
| Background | 0.020 | 0.020 | 0.030 | 0.030 |

Values in the table show OD. 492 nm.
ELISA-1: Improved solid phase ELISA of the present invention.
ELISA-2: Conventionally used solid phase ELISA

EXAMPLE 3

Antigen Specificity of Anti-TCF-II Antibody of the Present Invention

The improved solid phase ELISA obtained in Example 2 was used and hybridoma producing monoclonal antibody which exhibits affinity only to TCF-II without any affinity to HGF was screened. The result indicated that the appearance rate of hybridoma which produce the aimed antibody was about 5% and the others were all hybridomas producing antibodies which equally recognize both antigens. Hybridomas producing anti-TCF-II specific antibodies and typical hybridomas producing antibodies which equally recognize both TCF-II and HGF were respectively established by cloning 3–5 times using limit dilution method and above mentioned solid phase ELISA. The results are shown in Table 2. TCF-II , TCF-II reduced with 2-mercaptoethanol, TCF-II mutant with a deletion of all N-linked sugar chains constructed by protein engineering and HGF were respectively used as an antigen and their affinity (reactivity) was investigated by the modified ELISA. The results are shown in Table 3 as mentioned below. If an antibody which reacts solely with TCF-II is an antibody which recognizes peptide sequences or sugar chain moieties of the protein portion of TCF-II , the antibody must recognize the reduced TCF-II (red TCF-II ), whose steric structure is destroyed through only cleavage of S—S bond by treatment with reducing agents, as well as TCF-II.

However, as shown in Table 3, all antibodies of the present invention did not recognize the red TCF-II at all as well as HGF. Furthermore, all antibodies of the present invention bind to TCF-II mutant (mTCF-II ), which was prepared by removing all N-linked sugar chains (four chains in one molecule) by protein engineering, with the same affinity as TCF-II . Thus, the antibodies of the present invention are different from antibodies which recognize peptide sequences or sugar chains of TCF-II . As described above in detail, the monoclonal antibodies of the present invention exhibit affinity solely to TCF-II without any affinity to HGF and recognize three dimensionally formed epitope(s) which does not exist in HGF molecule and exist only in TCF-II molecule. In other words, the antibody of the present invention is an antibody which recognize the differences of steric structures between TCF-II and HGF. The antigen specificity of anti-TCF-II monoclonal antibodies, P5A8, P2D6 and P1C8, disclosed in Japanese Laid-open Patent Application No. 97 (1993) was investigated. As clearly shown in Table 3, these antibodies equally recognized TCF-II and HGF and the antibodies of the present invention clearly exhibited the different antigen specificity. As anti-TCF-II specific antibodies, A2G9, H9E3 and G10D1 were selected and their producing hybridoma strains were named A2G9, H9E3 and G10D1, respectively, and deposited on Feb. 8, 1994 to the National Institute of Bioscience and Human-Technology, Agency of Industrial Science and Technology Ministry of International Trade and Industry, 1–3, Higashi 1-chome, Tsukuba-shi, Ibaraki-ken 305 Japan as FERM P-14130 (FERM BP-4910), FERM P-14131 (FERM BP-4911) and FERM P-14132 (FERM BP-4912), respectively.

TABLE 2

Established typical hybridomas producing anti-TCF- II specific monoclonal antibodies which are solely reactive with TCF- II and non-reactive with HGF, and producing monoclonal antibodies which are equally reactive with both TCF- II and HGF.

| A. Monoclonal antibody solely reactive with TCF- II and non-reactive with HGF | | B. Monoclonal antibody equally reactive with both TCF- II and HGF | |
|---|---|---|---|
| Hybridoma strain | Specificity | Hybridoma strain | Specificity |
| 1. G10D1 | TCF- II | 1. 3P2D6 | TCF- II = HGF |
| 2. H9E3 | TCF- II | 2. 4B4A2 | TCF- II = HGF |
| 3. A2G9 | TCF- II | 3. 6B7D3 | TCF- II = HGF |
| | | 4. 4D12A7 | TCF- II = HGF |
| | | 5. 1A7B6 | TCF- II = HGF |
| | | 6. 3C11D7 | TCF- II = HGF |
| | | 7. 6H1D1 | TCF- II = HGF |
| | | 8. C4F8 | TCF- II = HGF |
| | | 9. 5B4F4 | TCF- II = HGF |
| | | 10. Y2G3B7 | TCF- II = HGF |
| | | 11. Y3H3H5 | TCF- II = HGF |
| | | 12. 1H4A1 | TCF- II = HGF |

TABLE 3

Affinity of antibodies produced by established hybridoma to various antigens and antigen specificity of monoclonal antibodies anti-TCF- II disclosed in Japanese Laid-open Patent Application No. 97 (1993).

| | Hybridoma culture medium | Antigen (OD. 492 nm) | | | |
|---|---|---|---|---|---|
| | | TCF- II | mTCF- II | red TCF- II | HGF |
| A | A2G9 | 1.195 | 1.229 | 0.070 | 0.075 |
| | | 1.426 | ND | 0.020 | 0.020 |
| | H9E3 | 1.210 | 1.275 | 0.085 | 0.091 |
| | | 1.271 | ND | 0.026 | 0.032 |
| | G10D1 | 0.801 | 0.820 | 0.075 | 0.078 |
| | | 0.837 | ND | 0.080 | 0.083 |
| B | 3P2D6 | 1.097 | ND | 0.040 | 1.093 |
| | 4B4A2 | 1.020 | ND | 0.033 | 1.037 |
| C | P5A8 | 1.032 | ND | 0.026 | 1.020 |
| | P2D6 | 1.213 | ND | 0.026 | 1.190 |
| | P1C8 | 1.226 | ND | 0.026 | 1.275 |

A: Antibodies of the present invention.
B: Antibodies equally reactive with TCF- II and HGF.
C: Antibodies disclosed in Japanese Laid-open Patent Application No. 97 (1993).
Background (OD. 492 nm): 0.02–0.090.
ND: Not determined.
mTCF- II: TCF- II mutant with a deletion of all N-linked sugar chains of TCF- II, constructed by protein engineering. TCF mutant was obtained by insertion of CDNA into an expression vector in a same way as that of Example 1 and expressed in cultured animal cells followed by purification in the same way as that of Example 1. mTCF-II has in vitro biological activity nearly equal to that of TCF- II.
red TCF- II: TCF- II reduced with 2-mercaptoethanol.

EXAMPLE 4

Production and Purification of Monoclonal Antibody

Materials: Hybridoma, 3 strains (A2G9, H9E3 and G10D1 in Table 2) producing anti-TCF-II specific monoclonal antibodies which react only with TCF-II without any reactivity with HGF and were obtained by Example 3.

Hybridoma, 2 strains (3P2D6 and 4B4A2 in Table 2) producing anti-TCF-II monoclonal antibodies which react equally with both antigens.

BALB/c mouse, 15 for one strain

Method: Each strain was transplanted intraperitoneally to mice given Pristane (Aldrich Chemical Co., Inc.) at a cell density of $1\times10^6$ cells/mouse. The accumulated ascite was collected 10–14 days after the transplantation and the ascites containing anti-TCF-II specific monoclonal antibody of the present invention, and the monoclonal antibody which recognizes both TCF-II and HGF equally were respectively obtained. Purified antibodies were obtained by Affigel protein A Sepharose$^{RTM}$ chromatography (BioRad Co., Ltd.) according to the manual. That is, the ascite was diluted with equal volume of a binding buffer (BioRad Co., Ltd.) and charged to protein A column. The column was washed with a sufficient volume of the binding buffer and eluted with an elution buffer (BioRad Co., Ltd.). The eluate was dialyzed against PBS or water, and the protein content was determined by the method of Lowry using mouse IgG (BioRad Co., Ltd.), as a standard protein. The purity of purified antibody was analyzed by SDS-PAGE and a homogenous band showing molecular weight of about 150,000 was detected.

EXAMPLE 5

The class and subclass of the antibody of the present invention obtained by Example 4 and the antibody which equally recognize both TCF-II and HGF were tested using an immunoglobulin class and subclass analysis kit (Amersham Co., Ltd.). The procedure was carried out according to the protocol disclosed in the directions. The results are shown in Table 4. The antibody of the present invention, A2G9 and H9E3 belonged to $IgG_1$ and the antibody G10D1 belonged to $IgG_{2a}$. The light chain of all antibodies was κ chain.

TABLE 4

Analysis of class and subclass of the antibodies of the present invention which recognize only TCF- II without recognizing HGF, and antibodies which equally recognize both TCF- II and HGF.

| | Monoclonal antibody | $IgG_1$ | $IgG_{2a}$ | $IgG_{2b}$ | $IgG_3$ | IgA | IgM | κ |
|---|---|---|---|---|---|---|---|---|
| A | A2G9 | + | − | − | − | − | − | + |
| | H9E3 | + | − | − | − | − | − | + |
| B | G10D1 | − | + | − | − | − | − | + |
| | 3P2D6 | + | − | − | − | − | − | + |
| | 4B4A2 | + | − | − | − | − | − | + |

A: Antibodies which recognize only TCF- II but not recognize HGF.
B: Antibodies which equally recognize both TCF- II and HGF.

EXAMPLE 6

Specificity of Sandwich ELISA Employing Monoclonal Antibody of the Present Invention Which Recognizes only TCF-II but not HGF at all The anti-TCF-II antibodies, A2G9, H9E3 and G10D1 of the present invention which were obtained by Example 4 and react only with TCF-II, but not with HGF were used as solid phase antibodies. These antibodies were used to construct sandwich ELISA in combination with an enzyme labeled antibody, 3P2D6 which equally recognizes both TCF-II and HGF. Control sandwich ELISA was constructed by using the representative antibody, 4B4A2, which equally react with both TCF-II and HGF, as solid phase antibody and using 3P2D6 as an enzyme labeled antibody. The specificity of these sandwich ELISA was investigated. Enzyme labeling of 3P2D6 with peroxidase (POD) was carried out according to the method of Ishikawa et al. (Ishikawa, E. et al.: J. Immunoassay, 4, 209–327, 1983). The antibody used for solid phase antibody was dissolved in 0.1M NaHCO$_3$ to give final concentration of 10 μg/ml and 100 μl of the solution was added to each well in 96-well immunoplates (Nunc Co., Ltd.) and the immunoplates were allowed to stand at room temperature overnight. Then, 200 μl of 50% Blockace$^{RTM}$ was added to each well in the plate and the plates were allowed to stand at room temperature for one hour to ensure blocking. The wells were washed three times with a washing buffer of PBS containing 0.1% Tween$^{RTM}$ 20.

The purified TCF-II or HGF was serially diluted with 1st reaction buffer (0.2M Tris-HCl buffer, pH 7.4, containing 40% Blockace$^{RTM}$ and 0.1% Tween$^{RTM}$ 20) to prepare sample solutions for determination (0–200 μg/ml of TCF-II or HGF/ml). To each well, 100 μl each of the sample solution was added and the immunoplates were allowed to stand at 37° C. for three hours, subsequently washed three times with the washing buffer. Then, 100 μl of diluted POD labeled 3P2D6 antibody 2,500-fold with 2nd reaction buffer (0.1M Tris-HCl buffer, pH 7.4, containing 25% Blockace$^{RTM}$ and 0.1% Tween$^{RTM}$ 20) was added to each well, and the immunoplates were allowed to stand at 37° C. for two hours, then washed three times with the washing buffer. Thereafter, 100 μl of an enzyme substrate solution (0.1M citrate-phosphate buffer, pH 4.5, containing 0.4 mg/ml of o-phenylenediamine. HCl and 0.006% H$_2$O$_2$) was added to each well. After the immunoplates were allowed to stand at 37° C. for 30 min., 50 μl of 6N H$_2$SO$_4$ was added to terminate the enzymatic reaction and the optical density (OD) at 492 nm of each well was determined using Immunoreader$^{RTM}$ (Corona Co., Ltd.)

Figure 4:
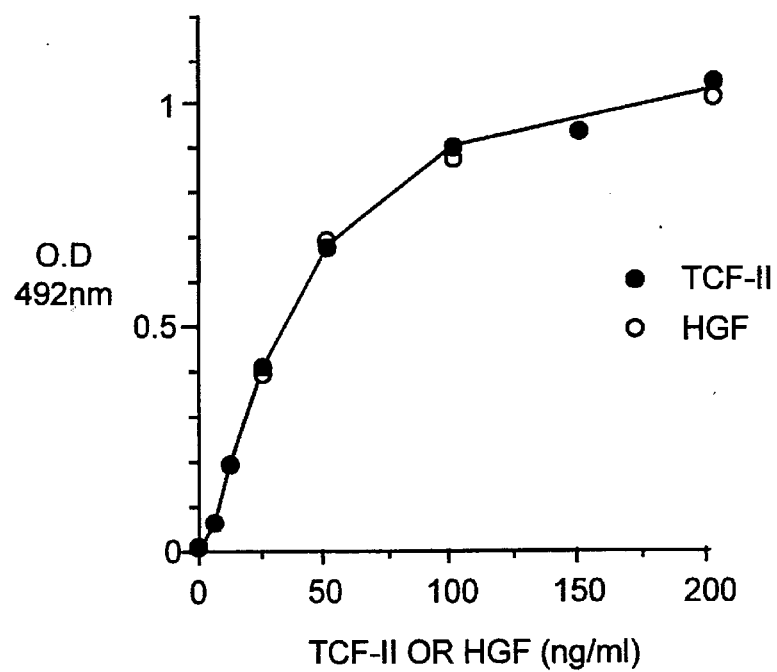
FIG. 4 shows the determination curves of TCF-II and HGF with the combination of antibody 4B4A2 of Example 6 and POD-labeled 3P2D6 (Control group).

The results of determination of TCF-II and HGF in combination of each antibody are shown in FIG. 1–4. FIG. 4 shows the results of determination of TCF-II and HGF in sandwich ELISA constructed by using an antibody 4B4A2, which equally recognizes both TCF-II and HGF, as a solid phase antibody and an antibody, 3P2D6, which equally recognizes both antigens, as a POD-labeled antibody. The determination curves of TCF-II and HGF were completely identical. However, sandwich ELISA, which was constructed by using the antibodies of the present invention, A2G9 (FIG. 1), H9E3 (FIG. 2) and G10D1 (FIG. 3), which recognize TCF-II only, as solid phase antibodies and by using an antibody, 3P2D6, which equally recognizes both TCF-II and HGF, as a POD-labeled antibody showed a determination curve only for TCF-II. Therefore, quantitative determination could be carried out only for TCF-II in the sandwich ELISA. While HGF showed no response even at a high concentration of 200 ng/ml and its optical density at OD 492 nm was the same as that of the background. These results revealed that sandwich ELISA, which was constructed by using anti-TCF-II specific antibody of the present invention as a solid phase antibody and the antibody, which equally recognizes both TCF-II and HGF, as a POD-labeled antibody was specific to TCF-II. The following Examples were carried out by using sandwich ELISA composed of a set of solid phase antibody, H9E3 and enzyme-labeled antibody, 3P2D6, as a typical antibody combination which specifically determine only TCF-II, and by using sandwich ELISA composed of a set of solid phase antibody, 4B4A2 and enzyme-labeled antibody, 3P2D6 as an antibody combination which can determine both TCF-II and HGF equally.

EXAMPLE 7

Selective Quantitative Determination of TCF-II and HGF in Human Sera

Normal human sera were screened to give serum containing TCF-II and HGF at levels of less than detection limit by ELISA in combination of 4B4A2 and 3P2D6 and the obtained serum is supplemented with various combinations of TCF-II and HGF at known concentrations. Whether the sandwich ELISA by a combination of H9E3 and 3P2D6 can selectively and quantitatively determine TCF-II in serum regardless of the presence of HGF, and the combinational use of the former ELISA and an ELISA constructed by the combination of 4B4A2 and 3P2D6 makes it possible to quantitatively determine HGF were investigated.

That is, human serum was supplemented with purified TCF-II and HGF obtained by Example 1 at various concentrations. TCF-II and total amount of antigens of TCF-II and HGF in the serum were quantitatively determined by (a) sandwich ELISA constructed by a combination of H9E3 and 3P2D6, and (b) sandwich ELISA constructed by a combination of 4B4A2 and 3P2D6, respectively. In addition, whether the subtraction of (a) from (b) gives the content of HGF in the serum was investigated.

H9E3 (10 μg/ml in 0.1M NaHCO$_3$) and 4B4A2 (10 μg/ml in 0.1M NaHCO$_3$) were respectively used as solid phase antibodies, and a 96-well immunoplate was coated with H9E3 or 4B4A2 in a similar manner with that of Example 5. Each plate was blocked with Blockace$^{RTM}$ in a similar manner and washed three times with the washing buffer.

The determination curve was prepared by using TCF-II as an antigen and diluting TCF-II with a buffer (PBS containing 50% Blockace$^{RTM}$ and 0.1% Tween$^{RTM}$ 20, pH 7.3) at a series of concentrations (0–100 ng/ml). To each well coated with H9E3 or 4B4A2, 50 μl of 1st reaction buffer (0.1M Tris-HCl buffer containing 50% Blockace$^{RTM}$, 0.2M NaCl, 0.1% Tween$^{RTM}$ 20, 2% CHAPS, 20 mM benzamine. HCl and 10 mM EDTA) and 50 μl of TCF-II prepared as above was successively added, and then mixed well. The immunoplates were incubated at 37° C. for three hours and washed three times. Then, POD-labeled 3P2D6 antibody was diluted 500-fold with 2nd reaction buffer (0.1M phosphate buffer containing 10% Blockace$^{RTM}$, 0.15M NaCl, 0.1% Tween$^{RTM}$ 20, 4% rat serum and 500 μg/ml mouse IgG, pH 7.0), 100 μl of the diluted solution was added to each well in 96-well immunoplates and the immunoplates were incubated at 37° C. for two hours. After each well was washed three times with the washing buffer, 100 μl of a substrate solution (0.1M citrate-phosphate buffer containing 0.4 mg/ml of o-phenylenediamine. HCl and 0.006% H$_2$O$_2$, pH 4.5) was added to each well and the immunoplates were incubated at 37° C. for 30 min. The determination curves of a TCF-II specific ELISA (a) constructed by the combination of H9E3 and 3P2D6, and an ELISA (b), which equally recognizes both TCF-II and HGF and was constructed by the combination of 4B4A2 and 3P2D6, showed linearity in the range of 0.1–50 ng/ml of antigen, (TCF-II).

In the ELISA shown above, human serum containing various known concentrations of TCF-II and HGF was added to each well instead of the TCF-II standard solution and similar procedure was carried out to recover the amount of antigen of TCF-II and total amount of antigens (TCF-II+ HGF). The results are shown in Table 5 as mentioned below.

Regardless of the extent of co-existing of HGF, selective determination of TCF-II became possible by application of ELISA constructed by the combination of a solid phase antibody of anti-TCF-II specific antibody of the present invention and an enzyme-labeled antibody which equally recognize both TCF-II and HGF. The amount of HGF can be determined by subtracting the amount of TCF-II from the total amount of antigens obtained by an ELISA constructed by the combination of a solid phase antibody and enzyme-labeled antibody which equally recognize both TCF-II and HGF.

TABLE 5

Quantitative and selective recovery of TCF- II and HGF from human serum added various combinations of known amounts of TCF- II and HGF.

| Human serum sample | Added Total antigen ng/ml | Added TCF- II ng/ml | Added HGF ng/ml | Recovered ELISA (b) Total antigen ng/ml (A) | Recovered ELISA (a) TCF- II ng/ml (B) | (A)-(B) ng/ml | HGF Theoretical value ng/ml |
|---|---|---|---|---|---|---|---|
| 1 | 50.0 | 25.00 | 25.00 | 50.5 | 25.50 | 25.00 | 25.00 |
| 2 |  | 12.50 | 37.50 |  | 13.25 | 37.25 | 37.50 |
| 3 |  | 37.50 | 12.50 |  | 37.25 | 13.25 | 12.50 |
| 4 | 25.0 | 12.50 | 12.50 | 23.5 | 12.50 | 11.00 | 12.50 |
| 5 |  | 6.25 | 18.75 |  | 6.00 | 17.50 | 18.75 |
| 6 |  | 18.75 | 6.25 |  | 18.50 | 5.00 | 6.25 |
| 7 | 12.5 | 6.25 | 6.25 | 12.0 | 6.25 | 5.75 | 6.25 |
| 8 |  | 3.13 | 9.37 |  | 3.25 | 8.75 | 9.37 |
| 9 |  | 9.37 | 3.13 |  | 9.25 | 2.75 | 3.13 |
| 10 | 5.0 | 2.50 | 2.50 | 4.9 | 2.50 | 2.40 | 2.50 |
| 11 |  | 1.25 | 3.75 |  | 1.50 | 3.40 | 3.75 |
| 12 |  | 3.75 | 1.25 |  | 3.75 | 1.15 | 1.25 |
| 13 | 2.0 | 1.00 | 1.00 | 2.0 | 1.20 | 0.80 | 1.00 |
| 14 |  | 0.50 | 1.50 |  | 0.55 | 1.45 | 1.50 |
| 15 |  | 1.50 | 0.50 |  | 1.55 | 0.45 | 0.50 |
| 16 | 1.0 | 0.50 | 0.50 | 1.0 | 0.50 | 0.50 | 0.50 |
| 17 |  | 0.25 | 0.75 |  | 0.25 | 0.75 | 0.75 |
| 18 |  | 0.75 | 0.25 |  | 0.80 | 0.20 | 0.20 |
| 19 | 0 |  |  |  |  |  |  |

EXAMPLE 8

Selective Purification of TCF-II from Cell Culture Medium Containing TCF-II and HGF Selective purification of TCF-II from culture medium of two liters, which was prepared by mixing one liter each of culture media containing five µg/ml of TCF-II and containing four µg/ml of HGF obtained in Example 1, was performed by immunoabsorbent affinity chromatography using monoclonal antibody G10D1 of the present invention. Preparation of immobilized G10D1 was performed by using Affigel$^{RTM}$ 10 (BioRad Co., Ltd.) as a mixture, and according to the attached manual to give four mg G10D1/ml gel.

To the mixed cell culture medium of two liters, 15 ml of G10D1 immobilized gel was added and stirred overnight at 4° C. to adsorb TCF-II. The mixture was filtered using a Büchner funnel and the collected gel was packed into a column (2×10 cm), extensively washed with PBS and TCF-II was eluted from the column with 0.1M glycine-HCl buffer, pH 2.5–3.0. The eluate was collected in test tubes containing 1M Tris-HCl buffer, pH 8.5, and immediately neutralized. The amount of TCF-II in 30 ml of the eluate was determined by an ELISA, which is specific for determination of TCF-II, shown in Example 6 and by an ELISA which equally recognizes TCF-II and HGF. Both ELISAs gave about 4.6 mg of TCF-II. Similar determination by the TCF-II specific ELISA showed scarcely any antigen in culture medium after treatment with immunosorbent gel, but an ELISA which equally recognizes both TCF-II and HGF detected about two µg/ml of antigen (HGF) in the culture medium. The application of the antibody of present invention to immunoabsorbent affinity chromatography led to success in selective purification of TCF-II with high yield (about 92%) and without any disturbance of the presence of HGF.

[Sequence Table]

Sequence number: 1
Length of sequence: 723
Type of sequence: amino acids
Group of sequence: protein
Sequence

| Met 1 | Trp | Val | Thr | Lys 5 | Leu | Leu | Pro | Ala | Leu 10 | Leu | Leu | Gln | His | Val 15 |
|---|---|---|---|---|---|---|---|---|---|---|---|---|---|---|
| Leu | Leu | His | Leu | Leu 20 | Leu | Leu | Pro | Ile | Ala 25 | Ile | Pro | Tyr | Ala | Glu 30 |
| Gly | Gln | Arg | Lys | Arg 35 | Arg | Asn | Thr | Ile | His 40 | Glu | Phe | Lys | Lys | Ser 45 |
| Ala | Lys | Thr | Thr | Leu 50 | Ile | Lys | Ile | Asp | Pro 55 | Ala | Leu | Lys | Ile | Lys 60 |
| Thr | Lys | Lys | Val | Asn 65 | Thr | Ala | Asp | Gln | Cys 70 | Ala | Asn | Arg | Cys | Thr 75 |
| Arg | Asn | Lys | Gly | Leu 80 | Pro | Phe | Thr | Cys | Lys 85 | Ala | Phe | Val | Phe | Asp 90 |
| Lys | Ala | Arg | Lys | Gln 95 | Cys | Leu | Trp | Phe | Pro 100 | Phe | Asn | Ser | Met | Ser 105 |
| Ser | Gly | Val | Lys | Lys 110 | Glu | Phe | Gly | His | Glu 115 | Phe | Asp | Leu | Tyr | Glu 120 |
| Asn | Lys | Asp | Tyr | Ile 125 | Arg | Asn | Cys | Ile | Ile 130 | Gly | Lys | Gly | Arg | Ser 135 |
| Tyr | Lys | Gly | Thr | Val 140 | Ser | Ile | Thr | Lys | Ser 145 | Gly | Ile | Lys | Cys | Gln 150 |
| Pro | Trp | Ser | Ser | Met 155 | Ile | Pro | His | Glu | His 160 | Ser | Tyr | Arg | Gly | Lys 165 |

-continued

[Sequence Table]

Asp Leu Gln Gln Asn Tyr Cys Arg Asn Pro Arg Gly Glu Glu Gly
                    170             175                 180

Gly Pro Trp Cys Phe Thr Ser Asn Pro Glu Val Arg Tyr Glu Val
                185             190                 195

Cys Asp Ile Pro Gln Cys Ser Glu Val Glu Cys Met Thr Cys Asn
                200             205                 210

Gly Glu Ser Tyr Arg Gly Leu Met Asp His Thr Glu Ser Gly Lys
                215             220                 225

Ile Cys Gln Arg Trp Asp His Gln Thr Pro His Arg His Lys Phe
                230             235                 240

Leu Pro Glu Arg Tyr Pro Asp Lys Gly Phe Asp Asp Asn Tyr Cys
                245             250                 255

Arg Asn Pro Asp Gly Gln Pro Arg Pro Trp Cys Tyr Thr Leu Asp
                260             265                 270

Pro His Thr Arg Trp Glu Tyr Cys Ala Ile Lys Thr Cys Ala Asp
                275             280                 285

Asn Thr Met Asn Asp Thr Asp Val Pro Leu Glu Thr Thr Glu Cys
                290             295                 300

Ile Gln Gly Gln Gly Glu Gly Tyr Arg Gly Thr Val Asn Thr Ile
                305             310                 315

Trp Asn Gly Ile Pro Cys Gln Arg Trp Asp Ser Gln Tyr Pro His
                320             325                 330

Glu His Asp Met Thr Pro Glu Asn Phe Lys Cys Lys Asp Leu Arg
                335             340                 345

Glu Asn Tyr Cys Arg Asn Pro Asp Gly Ser Glu Ser Pro Trp Cys
                350             355                 360

Phe Thr Thr Asp Pro Asn Ile Arg Val Gly Tyr Cys Ser Gln Ile
                365             370                 375

Pro Asn Cys Asp Met Ser His Gly Gln Asp Cys Tyr Arg Gly Asn
                380             385                 390

Gly Lys Asn Tyr Met Gly Asn Leu Ser Met Thr Arg Ser Gly Leu
                395             400                 405

Thr Cys Ser Met Trp Asp Lys Asn Met Glu Asp Leu His Arg His
                410             415                 420

Ile Phe Trp Glu Pro Asp Ala Ser Lys Leu Asn Glu Asn Tyr Cys
                425             430                 435

Arg Asn Pro Asp Asp Asp Ala His Gly Pro Trp Cys Tyr Thr Gly
                440             445                 450

Asn Pro Leu Ile Pro Trp Asp Tyr Cys Pro Ile Ser Arg Cys Glu
                455             460                 465

Gly Asp Thr Thr Pro Thr Ile Val Asn Leu Asp His Pro Val Ile
                470             475                 480

Ser Cys Ala Lys Thr Lys Gln Leu Arg Val Val Asn Gly Ile Pro
                485             490                 495

Thr Arg Thr Asn Ile Gly Trp Met Val Ser Leu Arg Tyr Arg Asn
                500             505                 510

Lys His Ile Cys Gly Gly Ser Leu Ile Lys Glu Ser Trp Val Leu
                515             520                 525

Thr Ala Arg Gln Cys Phe Pro Ser Arg Asp Leu Lys Asp Tyr Glu
                530             535                 540

Ala Trp Leu Gly Ile His Asp Val His Gly Arg Gly Asp Glu Lys
                545             550                 555

Cys Lys Gln Val Leu Asn Val Ser Gln Leu Val Tyr Gly Pro Glu
                560             565                 570

-continued
[Sequence Table]

| | | | | | | | | | | | | |
|---|---|---|---|---|---|---|---|---|---|---|---|---|
| Gly | Ser | Asp | Leu 575 | Val | Leu | Met | Lys | Leu | Ala 580 | Arg | Pro | Ala | Val | Leu 585 |
| Asp | Asp | Phe | Val | Ser 590 | Thr | Ile | Asp | Leu | Pro 595 | Asn | Tyr | Gly | Cys | Thr 600 |
| Ile | Pro | Glu | Lys | Thr 605 | Ser | Cys | Ser | Val | Tyr 610 | Gly | Trp | Gly | Tyr | Thr 615 |
| Gly | Leu | Ile | Asn | Tyr 620 | Asp | Gly | Leu | Leu | Arg 625 | Val | Ala | His | Leu | Tyr 630 |
| Ile | Met | Gly | Asn | Glu 635 | Lys | Cys | Ser | Gln | His 640 | His | Arg | Gly | Lys | Val 645 |
| Thr | Leu | Asn | Glu | Ser 650 | Glu | Ile | Cys | Ala | Gly 655 | Ala | Glu | Lys | Ile | Gly 660 |
| Ser | Gly | Pro | Cys | Glu 665 | Gly | Asp | Tyr | Gly | Gly 670 | Pro | Leu | Val | Cys | Glu 675 |
| Gln | His | Lys | Met | Arg 680 | Met | Val | Leu | Gly | Val 685 | Ile | Val | Pro | Gly | Arg 690 |
| Gly | Cys | Ala | Ile | Pro 695 | Asn | Arg | Pro | Gly | Ile 700 | Phe | Val | Arg | Val | Ala 705 |
| Tyr | Tyr | Ala | Lys | Trp 710 | Ile | His | Lys | Ile | Ile 715 | Leu | Thr | Tyr | Lys | Val 720 |
| Pro | Gln | Ser 723 | | | | | | | | | | | | |

---

We claim:

1. A monoclonal antibody exhibiting affinity for human TCF-II and without any affinity for human HGF.

2. The monoclonal antibody according to claim 1 obtained from a culture medium of a hybridoma producing anti-TCF-II antibody with affinity for TCF-II but not with HGF said antibody further comprising the following properties:

a molecular weight of about 150,000 daltons, a subclass of IgG$_1$ or IgG$_{2a}$, and a light chain of κ chain.

3. Hybridomas producing an anti-TCF-II antibody with affinity for TCF-II and without affinity for HGF; said hybridomas being deposited as FERM BP-4910, FERM BP-4911 or FERM BP-4912 in the National Institute of Bioscience and Human-Technology, Agency of Industrial Science and Technology.

4. A method for selectively determining the presence of TCF-II in a sample suspected of containing TCF-II and HGF, said method comprising contacting the sample with an antibody according to claim 1 or 2 under conditions sufficient to form a TCF-II-antibody complex; and determining formation of said complex, thereby determining the presence of TCF-II.

5. A method for purifying TCF-II from a sample containing TCF-II and HGF comprising:

contacting said sample with an immobilized antibody according to claim 1 or 2 under conditions sufficient to form a TCF-II-antibody complex; separating the complex; and eluting TCF-II from said immobilized antibody.

6. A process for selecting a monoclonal antibody with affinity for TCF-II and without any affinity for HGF comprising diluting the culture medium of a hybridoma producing anti-TCF-II antibody about 2- to 4-fold with a blocking solution containing a surface active agent; contacting said diluted culture medium with immobilized TCF-II or HGF; and selecting for culture the hybridoma producing a monoclonal antibody with affinity to TCF-II and without any affinity to HGF.

7. The process for the selection of a monoclonal antibody according to claim 6 wherein the surface active agent is polyoxyethylene sorbitan monolaurate.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 723 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

| | | | | | | | | | | | | | | |
|---|---|---|---|---|---|---|---|---|---|---|---|---|---|---|
| Met 1 | Trp | Val | Thr | Lys 5 | Leu | Leu | Pro | Ala | Leu 10 | Leu | Leu | Gln | His | Val 15 | Leu |
| Leu | His | Leu | Leu 20 | Leu | Leu | Pro | Ile | Ala 25 | Ile | Pro | Tyr | Ala | Glu 30 | Gly | Gln |
| Arg | Lys | Arg 35 | Arg | Asn | Thr | Ile | His 40 | Glu | Phe | Lys | Lys | Ser 45 | Ala | Lys | Thr |
| Thr | Leu 50 | Ile | Lys | Ile | Asp | Pro 55 | Ala | Leu | Lys | Ile | Lys 60 | Thr | Lys | Lys | Val |
| Asn 65 | Thr | Ala | Asp | Gln | Cys 70 | Ala | Asn | Arg | Cys | Thr 75 | Arg | Asn | Lys | Gly | Leu 80 |
| Pro | Phe | Thr | Cys | Lys 85 | Ala | Phe | Val | Phe | Asp 90 | Lys | Ala | Arg | Lys | Gln 95 | Cys |
| Leu | Trp | Phe | Pro 100 | Phe | Asn | Ser | Met | Ser 105 | Ser | Gly | Val | Lys | Lys 110 | Glu | Phe |
| Gly | His | Glu 115 | Phe | Asp | Leu | Tyr | Glu 120 | Asn | Lys | Asp | Tyr | Ile 125 | Arg | Asn | Cys |

```
Ile  Ile  Gly  Lys  Gly  Arg  Ser  Tyr  Lys  Gly  Thr  Val  Ser  Ile  Thr  Lys
     130                 135                 140

Ser  Gly  Ile  Lys  Cys  Gln  Pro  Trp  Ser  Ser  Met  Ile  Pro  His  Glu  His
145                      150                 155                           160

Ser  Tyr  Arg  Gly  Lys  Asp  Leu  Gln  Glu  Asn  Tyr  Cys  Arg  Asn  Pro  Arg
                    165                 170                           175

Gly  Glu  Glu  Gly  Gly  Pro  Trp  Cys  Phe  Thr  Ser  Asn  Pro  Glu  Val  Arg
               180                 185                      190

Tyr  Glu  Val  Cys  Asp  Ile  Pro  Gln  Cys  Ser  Glu  Val  Glu  Cys  Met  Thr
          195                      200                 205

Cys  Asn  Gly  Glu  Ser  Tyr  Arg  Gly  Leu  Met  Asp  His  Thr  Glu  Ser  Gly
     210                 215                      220

Lys  Ile  Cys  Gln  Arg  Trp  Asp  His  Gln  Thr  Pro  His  Arg  His  Lys  Phe
225                      230                 235                           240

Leu  Pro  Glu  Arg  Tyr  Pro  Asp  Lys  Gly  Phe  Asp  Asp  Asn  Tyr  Cys  Arg
                    245                 250                      255

Asn  Pro  Asp  Gly  Gln  Pro  Arg  Pro  Trp  Cys  Tyr  Thr  Leu  Asp  Pro  His
               260                 265                      270

Thr  Arg  Trp  Glu  Tyr  Cys  Ala  Ile  Lys  Thr  Cys  Ala  Asp  Asn  Thr  Met
          275                 280                 285

Asn  Asp  Thr  Asp  Val  Pro  Leu  Glu  Thr  Thr  Glu  Cys  Ile  Gln  Gly  Gln
     290                 295                      300

Gly  Glu  Gly  Tyr  Arg  Gly  Thr  Val  Asn  Thr  Ile  Trp  Asn  Gly  Ile  Pro
305                      310                 315                           320

Cys  Gln  Arg  Trp  Asp  Ser  Gln  Tyr  Pro  His  Glu  His  Asp  Met  Thr  Pro
                    325                 330                      335

Glu  Asn  Phe  Lys  Cys  Lys  Asp  Leu  Arg  Glu  Asn  Tyr  Cys  Arg  Asn  Pro
               340                 345                      350

Asp  Gly  Ser  Glu  Ser  Pro  Trp  Cys  Phe  Thr  Thr  Asp  Pro  Asn  Ile  Arg
          355                 360                 365

Val  Gly  Tyr  Cys  Ser  Gln  Ile  Pro  Asn  Cys  Asp  Met  Ser  His  Gly  Gln
     370                 375                      380

Asp  Cys  Tyr  Arg  Gly  Asn  Gly  Lys  Asn  Tyr  Met  Gly  Asn  Leu  Ser  Gln
385                      390                 395                           400

Thr  Arg  Ser  Gly  Leu  Thr  Cys  Ser  Met  Trp  Asp  Lys  Asn  Met  Glu  Asp
                    405                 410                      415

Leu  His  Arg  His  Ile  Phe  Trp  Glu  Pro  Asp  Ala  Ser  Lys  Leu  Asn  Glu
               420                 425                      430

Asn  Tyr  Cys  Arg  Asn  Pro  Asp  Asp  Ala  His  Gly  Pro  Trp  Cys  Tyr
          435                 440                 445

Thr  Gly  Asn  Pro  Leu  Ile  Pro  Trp  Asp  Tyr  Cys  Pro  Ile  Ser  Arg  Cys
     450                 455                      460

Glu  Gly  Asp  Thr  Thr  Pro  Thr  Ile  Val  Asn  Leu  Asp  His  Pro  Val  Ile
465                      470                 475                           480

Ser  Cys  Ala  Lys  Thr  Lys  Gln  Leu  Arg  Val  Val  Asn  Gly  Ile  Pro  Thr
                    485                 490                      495

Arg  Thr  Asn  Ile  Gly  Trp  Met  Val  Ser  Leu  Arg  Tyr  Arg  Asn  Lys  His
               500                 505                      510

Ile  Cys  Gly  Gly  Ser  Leu  Ile  Lys  Glu  Ser  Trp  Val  Leu  Thr  Ala  Arg
          515                 520                 525

Gln  Cys  Phe  Pro  Ser  Arg  Asp  Leu  Lys  Asp  Tyr  Glu  Ala  Trp  Leu  Gly
     530                 535                      540

Ile  His  Asp  Val  His  Gly  Arg  Gly  Asp  Glu  Lys  Cys  Lys  Gln  Val  Leu
545                      550                 555                           560
```

-continued

```
Asn Val Ser Gln Leu Val Tyr Gly Pro Glu Gly Ser Asp Leu Val Leu
            565             570             575

Met Lys Leu Ala Arg Pro Ala Val Leu Asp Asp Phe Val Ser Thr Ile
            580             585             590

Asp Leu Pro Asn Tyr Gly Cys Thr Ile Pro Glu Lys Thr Ser Cys Ser
            595             600             605

Val Tyr Gly Trp Gly Tyr Thr Gly Leu Ile Asn Tyr Asp Gly Leu Leu
    610             615             620

Arg Val Ala His Leu Tyr Ile Met Gly Asn Glu Lys Cys Ser Gln His
625             630             635             640

His Arg Gly Lys Val Thr Leu Asn Glu Ser Glu Ile Cys Ala Gly Ala
            645             650             655

Glu Lys Ile Gly Ser Gly Pro Cys Glu Gly Asp Tyr Gly Gly Pro Leu
            660             665             670

Val Cys Glu Gln His Lys Met Arg Met Val Leu Gly Val Ile Val Pro
        675             680             685

Gly Arg Gly Cys Ala Ile Pro Asn Arg Pro Gly Ile Phe Val Arg Val
    690             695             700

Ala Tyr Tyr Ala Lys Trp Ile His Lys Ile Ile Leu Thr Tyr Lys Val
705             710             715             720

Pro Gln Ser
```